US00PP08207P

United States Patent [19]

VandenBerg

[11] Patent Number: Plant 8,207

[45] Date of Patent: Apr. 20, 1993

[54] CHRYSANTHEMUM PLANT NAMED POWER

[75] Inventor: Cornelis P. VandenBerg, Salinas, Calif.

[73] Assignee: Yoder Brothers, Inc., Barberton, Ohio

[21] Appl. No.: 756,838

[22] Filed: Sep. 9, 1991

[51] Int. Cl.[5] ..... A01H 5/00

[52] U.S. Cl. ..... Plt./74.1

[58] Field of Search ..... Plt./74.1

*Primary Examiner*—Howard J. Locker

*Attorney, Agent, or Firm*—Foley & Lardner

[57] ABSTRACT

A Chrysanthemum plant named Power particularly characterized by its flat capitulum form; daisy capitulum type; red-purple ray floret color; diameter across face of capitulum of 51 to 57 mm when fully opened, when grown as a single stem spray cut mum; flowering response under normal temperatures is 47 to 50 days after start of short days; plant height is 81 to 99 cm when grown with 6 to 7 long days prior to start of short days; peduncle length of the first lateral at flowering after removing the apical bud without growth regulator applications is 8 to 10 cm; peduncle length of the fourth lateral at flowering is 10 to 15 cm; and terminal spray formation, with compounding of the lower laterals.

3 Drawing Sheets

The present invention comprises a new and distinct cultivar of Chrysanthemum, botanically known as *Dendranthema gradiflora,* and referred to by the cultivar name Power.

Power, identified as 2491 (87-504002), was originated from a cross made by Cornelis P. VandenBerg in a controlled breeding program in Salinas, Calif., in 1986.

The female parent of Power was an unnamed seedling identified as 6016 (82-J20103) and described as a cut spray mum with a flat capitulum form; a daisy capitulum type; an orange-bronze ray floret color; a diameter of capitulum of 70 mm when fully open; flowering response to short days of 48 to 53 days; a plant height of 79 to 86 cm when grown with 6 to 7 long days prior to start of short days; a peduncle length of the first lateral of 5 to 8 cm and of the fourth lateral of 13 to 15 cm; and a terminal spray formation. The above characteristics are based on plants grown in Salinas, Calif. The female parent was discarded from all programs on Jan. 28, 1988.

The male parent of Power was the cultivar identified as Oreo, disclosed in U.S. Plant Pat. No. 6,882, and described as a cut spray mum with a flat capitulum form; a daisy capitulum type; a purple ray floret color; a diameter of capitulum of 70 to 73 mm; a flowering response of 47 to 58 days; a plant height of 91 to 102 cm when grown with 14 long days prior to start of short days; a peduncle length of the first lateral of 8 to 13 cm and of the fourth lateral of 15 to 18 cm; and a terminal spray formation. These characteristics are based on plants grown in Salinas, Calif.

Power was discovered and selected as one flowering plant within the progeny of the stated cross by Cornelis P. VandenBerg in January, 1988, in a controlled environment in Salinas, Calif.

The first act of asexual reproduction of Power was accomplished when vegetative cuttings were taken from the initial selection in March, 1988, in a controlled environment in Salinas, Calif., by technicians working under supervision of Cornelis P. VandenBerg.

Horticultural examination of controlled flowerings of successive plantings has shown that the unique combination of characteristics as herein disclosed for Power are firmly fixed and are retained through successive generations of asexual reproduction.

Power has not been observed under all possible environmental conditions. The phenotype may vary with variations in environment such as temperature, light intensity and daylength, without, however, any variance in the genotype.

The following observations, measurements and comparisons describe plants grown in Salinas, Calif., under greenhouse conditions which approximate those generally used in commercial greenhouse practice.

The following traits have been repeatedly observed and are determined to be basic characteristics of Power, which, in combination, distinguish this Chrysanthemum as a new and distinct cultivar:

1. Flat capitulum form.
2. Daisy capitulum type.
3. Red-purple ray floret color.
4. Diameter across face of capitulum of 51 to 57 mm when fully opened, when grown as a single stem spray cut mum.
5. Flowering response under normal temperature is 47 to 50 days after start of short days.
6. Plant height is 81 to 99 cm when grown with 6 to 7 long days prior to start of short days.
7. Peduncle length of the first lateral at flowering after removing the apical bud without growth regulator application is 8 to 10 cm; peduncle length of the fourth lateral at flowering is 10 to 15 cm.
8. Terminal spray formation, with compounding of the lower laterals.

The accompaning photographic drawings show typical inflorescence and leaf characteristics of Power, with colors being as nearly true as possible with illustrations of this type.

Sheet 1 is a color photograph of Power grown as a single stem spray cut mum.

Sheet 2 is a black and white photograph of three views of the influorescence of Power.

Sheet 3 is a black and white photograph showing the upper and under sides of the leaves of Power at 3 stages of development (mature, intermediate and immature).

In sheets 2 and 3 a measuring tape in centimeters has been added.

No commercial cultivars known to the inventor are similar in comparison to Power. However, because of its ray floret color and capitulum form and type Power could be compared with the cultivar identified as Accent, disclosed in U.S. Plant Pat. No. 3,945. Reference is made to attached Chart A, which compares certain characteristics of Power to the same characteristics of Accent.

Similar traits are capitulum form and type, and ray floret color, which is red-purple for both cultivars, although the ray floret color of Accent is significantly darker than the ray floret color of Power. Power has a much smaller diameter of capitulum, an earlier flowering response to short days, aa taller plant height, requiring less long das to obtain a commercially acceptable height, a longer peduncle length of the first lateral and a shorter peduncle length of the fourth lateral when compared with Accent.

In the following description color reference are made to The Royal Horticultural Society Colour Chart. The color values were determined on plant material grown as a single stem spray cut mum in Salinas, Calif., on Jan. 22, 1990.

Classification:

*Botanical.*—Dendranthema grandiflora cv. Power.

*Commercial.*—Daisy spray cut mum.

INFLORESCENCE

A. Capitulum

*Form.*—Flat.

*Type.*—Daisy.

*Diameter across face.*—51 to 57 mm when fully opened.

B. Corolla of ray florets:

*Color (general tonality from a distance of three meters).*—Red-purple.

*Color (upper surface).*—77B, fading to 78C to 78D.

*Color (under surface).*—Closest to 78C to 78D.

*Shape.*—Straight, oblong, slightly ribbed.

C. Corolla of disc florets:

*Color (mature).*—14A.

*Color (imature).*—144A to 144B.

D. Reproductive organs:

*Androecium.*—Present on disc florets only; no pollen.

*Gynoecium.*—Present on both ray and disc florets.

PLANT

A. General appearance:

*Height.*—81 to 99 cm when grown in Salinas with 6 to 7 long days prior to start of short days.

B. Foliage:

*Color (upper surface).*—147A.

*Color (under surface).*—147B.

*Shape.* —See photograph.

CHART A

COMPARISON OF POWER AND ACCENT

| CHARACTERISTIC | POWER | ACCENT |
|---|---|---|
| Ray floret color | Red-purple | Dark red-purple |
| Capitulum form and type | Flat daisy | Flat daisy |
| Diameter across face of capitulum | 51 to 57 mm | 70 to 91 mm |
| Flowering response | 47 to 50 days | 50 to 57 days |
| Plant height: | | |
| 6–7 long days | 81 to 99 cm | |
| 14 long days | | 58 to 102 cm |
| Peduncle length: | | |
| First lateral | 8 to 10 cm | 3 to 10 cm |
| Fourth lateral | 10 to 15 cm | 13 to 20 cm |

COMPARISONS MADE OF PLANTS GROWN AS SINGLE STEM SPRAY CUT MUMS IN SALINAS, CALIFORNIA

I claim:

1. A new and distinct Chrysanthemum plant named Power, as described and illustrated.

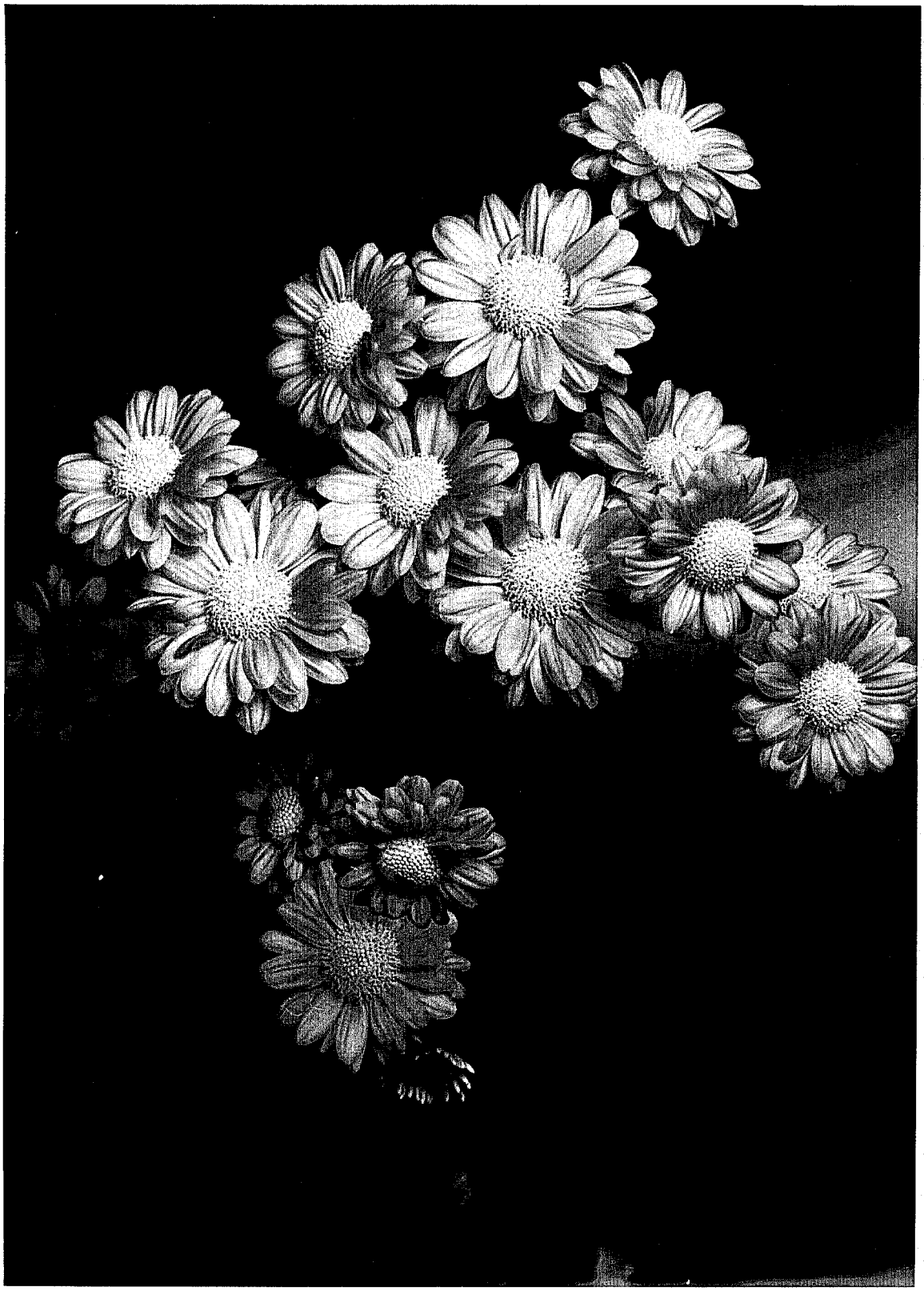

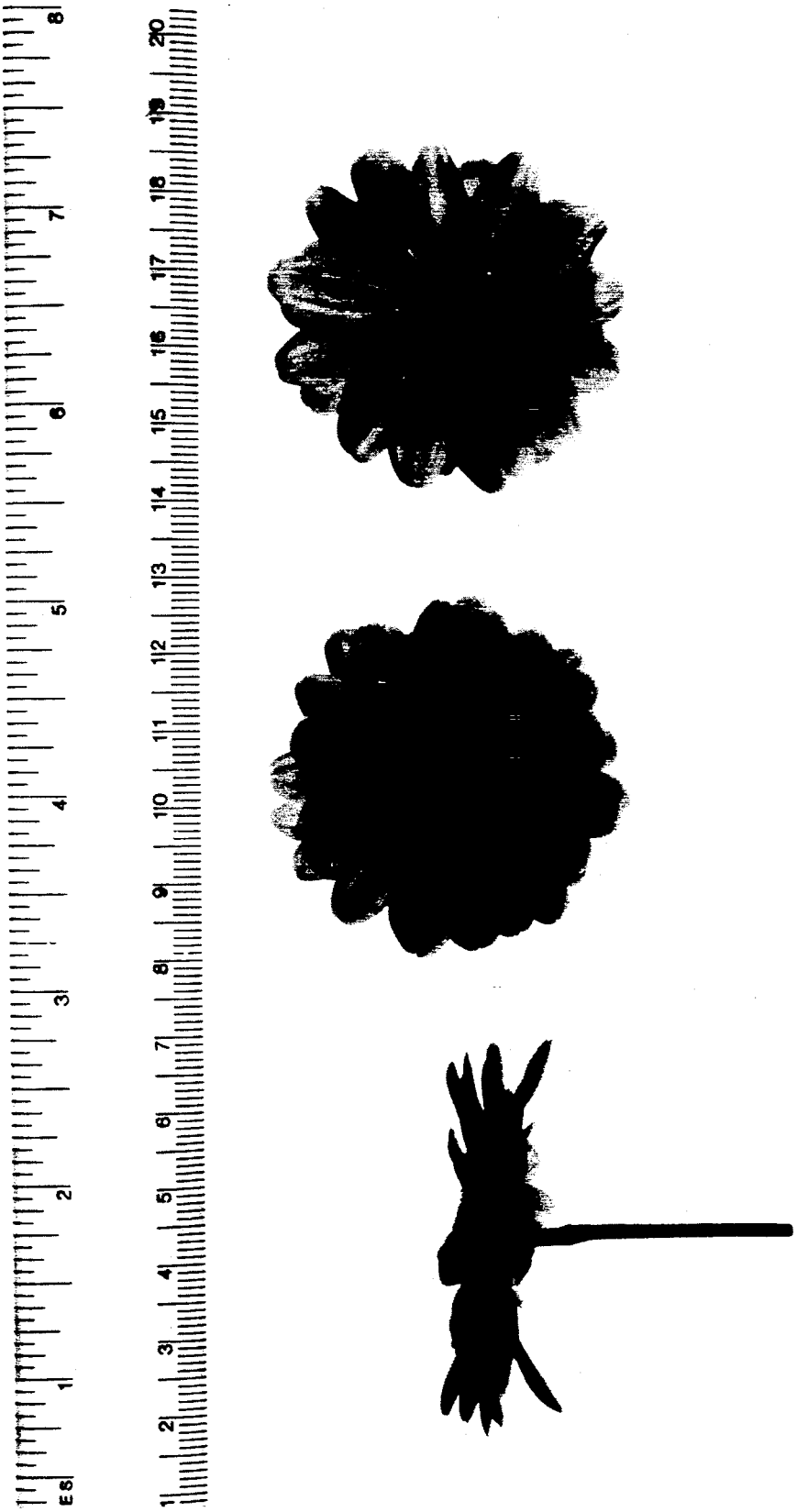

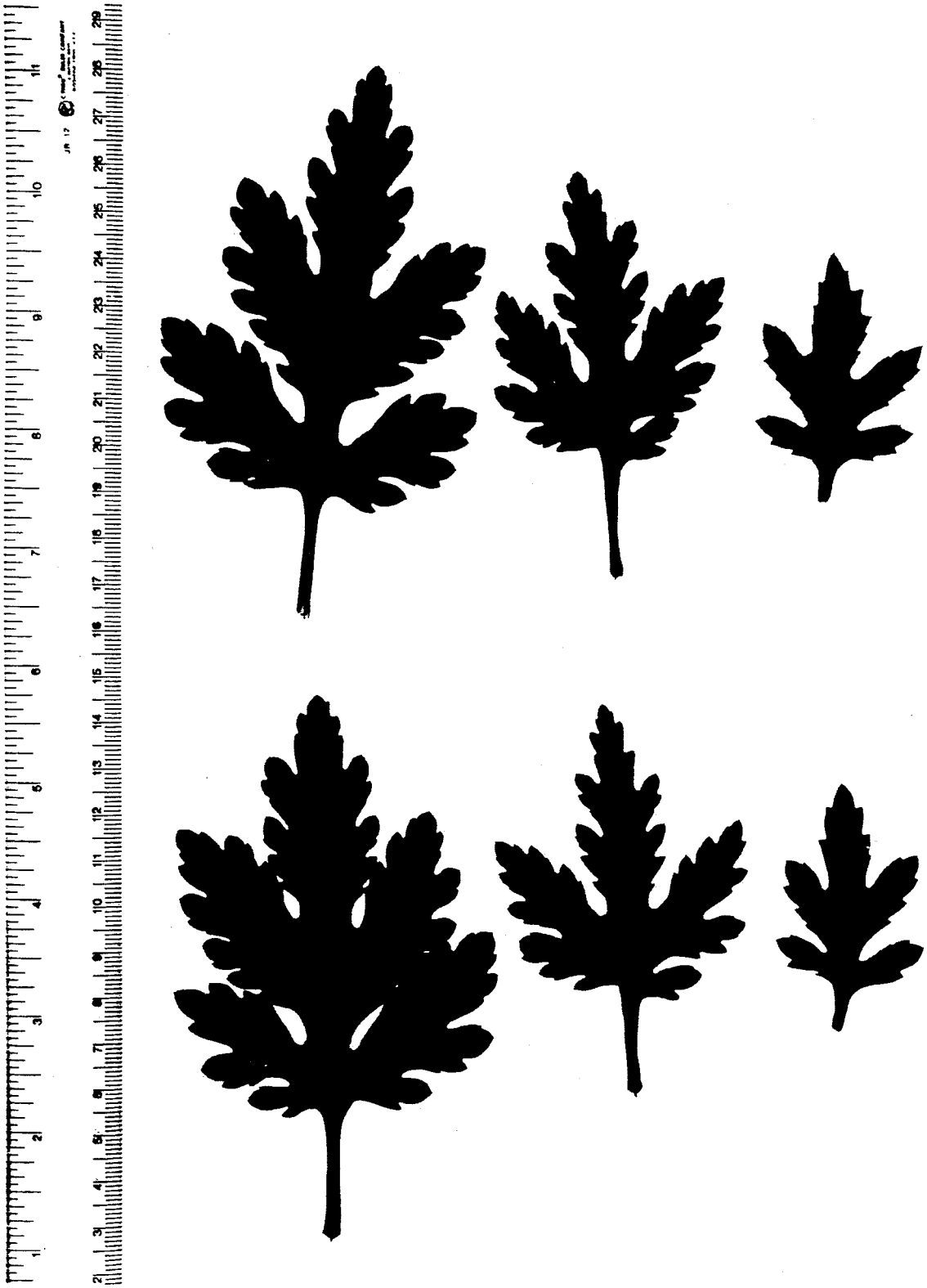

* * * * *